United States Patent [19]
Bettencourt et al.

[11] Patent Number: 5,164,065
[45] Date of Patent: Nov. 17, 1992

[54] NON-BREAKABLE, ELECTRICALLY INSULATING SAMPLE WELL INSERTS FOR SLAB ELECTROPHORESIS

[75] Inventors: Gregory Bettencourt, Fremont; George Fernwood, Larkspur, both of Calif.; Efrem G. Hernandez, Dallas, Tex.; Lin Crawforth, Fremont, Calif.

[73] Assignee: Bio-Rad Laboratories, Inc., Hercules, Calif.

[21] Appl. No.: 808,412

[22] Filed: Dec. 13, 1991

[51] Int. Cl.⁵ .................... G01N 27/26; B01D 57/02
[52] U.S. Cl. .......................... 204/299 R; 204/182.8
[58] Field of Search .......... 204/299 R, 182.8, 180.1, 204/182.7, 182.9

[56] References Cited

U.S. PATENT DOCUMENTS 3,932,265  1/1976  Hoefer ........................ 204/182.8
4,861,411  8/1989  Tezuka ........................ 204/299 R
4,909,918  3/1990  Bambeck et al. ............. 204/182.8
4,975,174  12/1990 Bambeck et al. ............. 204/299 R

FOREIGN PATENT DOCUMENTS 63-47648  2/1988  Japan ........................... 204/299 R Primary Examiner—John Niebling
Assistant Examiner—John S. Starsiak, Jr.
Attorney, Agent, or Firm—Townsend and Townsend

[57] ABSTRACT

Sharkstooth combs for use in slab electrophoresis for holding samples above the gel prior to being separated in contiguous lanes are formed of a metallic core sheathed in a surface coating to render such a comb electrically insulating. The metallic core provides the comb with the strength needed to prevent breakage of the teeth, which is otherwise a problem due to the thinness of the comb.

9 Claims, 1 Drawing Sheet

NON-BREAKABLE, ELECTRICALLY INSULATING SAMPLE WELL INSERTS FOR SLAB ELECTROPHORESIS

This invention lies in the field of vertical slab gel electrophoresis. In particular, this invention addresses problems associated with loading samples onto a slab gel, and with the use of "combs" to provide wells in which the multitude of samples are placed in preparation for the electrophoresis and to define the lanes which each sample will follow during its migration through the gel.

BACKGROUND OF THE INVENTION

Included among the many considerations in designing apparatus for vertical slab gel electrophoresis is the need to load samples in a reliable and reproducible manner, and in such a manner that a maximum number of samples can be separated simultaneously in a single gel, each with sharp band resolution.

Slab gels are usually formed by joining two glass plates together with spacers at both vertical edges to establish a gap between the plates which usually measures 0.25–3 mm in depth. The plates are clamped together along the vertical edges and a seal is placed along the open bottom edge. The gap is then filled with gel solution, and the gel is allowed to set. In some slab gels, a well-forming insert, referred to in the industry as a "comb" or a "template," is placed along the open upper edge of the gel solution before the gel sets, the teeth of the comb extending into the space between the plates. After the gel sets, the comb is removed to leave a row of wells formed in the gel along its top edge for example loading.

In other slab gels, particularly those ranging from 0.25–0.40 mm in thickness, a different type of comb is used, one which is placed between the gel plates after the gel has set and left in place during the electrophoresis. This comb is commonly referred to as a "sharkstooth comb" since its teeth are pointed and longer than those of the combs described above. Once the gel has been set, the comb is inserted between the plates such that the tips of the comb's teeth contact the upper edge of the gel. Between the teeth of the comb are inverted U-shaped spaces, each of which is used as a well to receive a sample which is to be subjected to an electrophoretic separation.

In structures where sharkstooth combs are used, the plates which hold the gel differ in height, with one plate extending a short distance above the other. The upper edge of the gel is located a short distance below the upper edge of the shorter plate. The sharkstooth comb is inserted between the plates in such a manner that the U-shaped spaces between the teeth extend above the shorter plate but not the taller plate, which closes them on one side. Liquid sample aliquots are then introduced into the spaces at their open sides, flowing into the area between the plates above the gel, where they form individual pools separated by the teeth. Since the teeth are narrow at their pointed ends, the samples although separated are very close together, forming essentially contiguous lanes.

The gels in which sharkstooth combs are used are generally very thin, and it is important that their thickness be uniform, since variations in thickness will affect the migration rates of the sample components and band resolution, and thus reproducibility as well as the ability of the results to be read and interpreted properly. The sharkstooth combs are likewise very thin, and inserting such a comb between glass plates which are so close together is a delicate procedure. The thinness of the combs as well as their sharply pointed teeth make the combs particularly delicate and susceptible to breakage.

SUMMARY OF THE INVENTION

Sharkstooth combs have heretofore been constructed only from electrically insulating polymeric materials to eliminate any possibility of interference of the combs with the electric field which is maintained during electrophoresis, and of forming bubbles in the electrode solution, the samples or the gel. Due to their delicate structures, these combs are prone to breakage. The present invention overcomes this problem by providing sharkstooth combs having a metallic core which offers a high resistance to breakage, the core being sheathed in a coating which provides electrical inertness to the comb.

DETAILED DESCRIPTION OF THE INVENTION AND PREFERRED EMBODIMENTS

Figure 1:
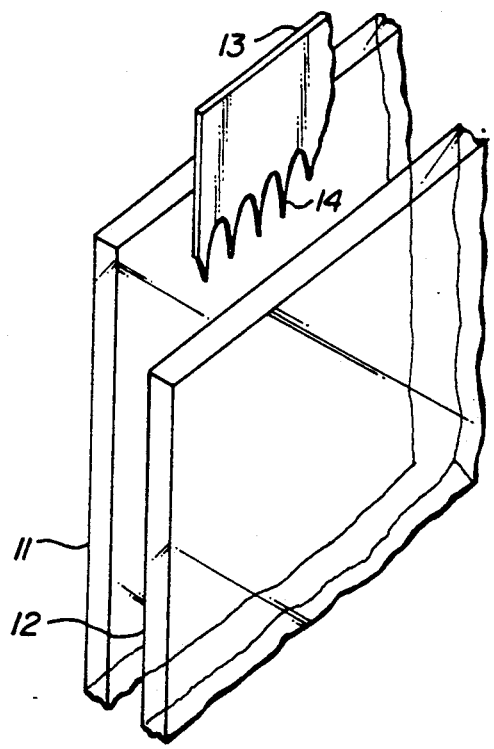
FIG. 1 is a perspective view of a sharkstooth comb of the present invention as it would be inserted between two glass plates holding a slab gel between them.

The metallic core of the comb in accordance with this invention may be any metal which is capable of being cut in thin sheets and which will maintain a flat shape with normal handling during use. Examples of metals which may be used are aluminum, stainless steel, copper and nickel. Aluminum is a preferred metal due to its strength, light weight, low cost and ability to bond to the polymeric coating.

The metallic core may be formed into the desired shape by any conventional means. Chemical etching is one particularly effective method.

The metallic core may be surface treated either to enhance the adherence of the coating or to reduce its electrical conductivity, or both. It is preferred that the metal be anodized, and anodized aluminum is a particularly preferred core metal.

The metallic core is sheathed in a coating of an electrically insulating material to eliminate any effects the comb may have on the electric field established by the applied voltage during electrophoresis. The coating will be of a material which is inert to aqueous acids and bases such as the buffer solutions used to establish contact between the gel and the electrodes which supply the voltage. Coatings of polymeric materials are practical and convenient. In a presently preferred embodiment, the coating is a layer of a polymer of p-xylylene or its derivatives (such as substituted p-xylylenes or compounds of similar structure). Polymers of this type may be applied to the metallic core by vapor-phase polymerization and vacuum deposition. These polymers are commercially available under the name Parylene, and the process of their formation and application is one which has been developed by Union Carbide Corporation, Danbury, Conn., U.S.A. The process of vapor-phase polymerization and deposition is particularly effective in forming uniform, thin films.

A specific example of a comb in accordance with this invention is one in which the core metal is 6061 aluminum, with a thickness of either 0.009 inch (0.023 cm) or 0.014 inch (0.036 cm), a length of 5.9 inch (15 cm), and a width of 1.1 inch (2.8 cm), with teeth defining either 24, 36 or 48 sample wells along the width. The length of each of the teeth is either 0.375 inch (0.95 cm) or 0.44 inch (1.12 cm). The combs are prepared by chemical etching, followed by hard anodizing, and coated with Parylene C (Viking Technology Inc. San Jose, Calif., U.S.A.) to a minimum thickness of 0.0005 inch (0.00127 cm) on all sides.

Turning now to the drawings, FIG. 1 is a perspective view of the two plates which are used to form the slab gel, and the comb. The two plates consist of a tall plate 11 and a short plate 12. The comb 13 is shown poised above the plates prior to being inserted. The teeth 14 of the comb are pointed down, as they will be when placed above the gel to form the sample wells.

Figure 2:
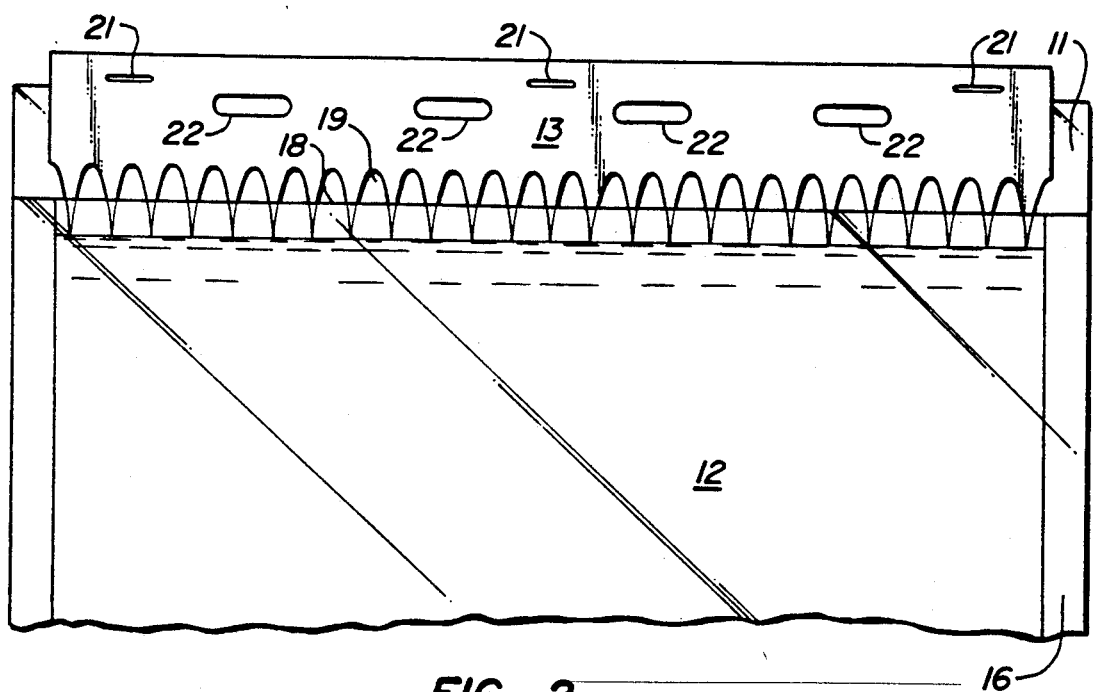
FIG. 2 is a front elevation view of the sharkstooth comb and glass plates of FIG. 1, together with the gel and spacers.

FIG. 2 is a front elevation view of the two plates 11 and 12 and the comb 13. The plates are separated by spacer strips 15, 16 along the side edges of the plates, the strips defining the width of the gel. The gel is also shown in this drawing, with its upper edge 17 below the upper edge 18 of the shorter plate 12. The U-shaped spaces 19 between the teeth extend above the upper edge 18 of the shorter plate to provide access for the placement of sample aliquots above the gel. As electrophoresis proceeds, the distances between the points of the teeth establish the widths of the lanes which will appear in the gel showing the separated bands corresponding to each sample.

Components which are not shown in these drawings are the clamps used to hold the two plates together, the support structure which holds the plates in the vertical position, and the electrode buffer reservoirs which contact the top and bottom edges of the gel. For the upper buffer reservoir, the taller plate 11 and comb 13 together form one side wall, and the U-shaped spaces 19 extending above the upper edge 18 of the shorter plate will be entirely immersed in the upper buffer solution.

Since the comb 13 has one straight edge 20 on the side opposite that of the teeth, this edge may be used to form the straight upper edge 18 of the gel while the gel is being cast. Using the comb in this manner, it will first be inverted (with the teeth pointing up) and its straight edge pushed down between the plates immediately after the gel solution has been poured in. A series of slits 21 arranged in a straight line a short distance from the straight edge 20 of the comb serve as visual guides to assure that the straight edge is held parallel to the upper edge of the shorter plate 11 while the gel is solidifying.

With the inverted comb in place (straight edge 20 down), the gel is allowed to set, the straight edge 20 thus serving to establish both the straightness and height of the upper edge of the gel. A further series of slits 22 is included in the comb to facilitate grasping of the comb so that it can be removed after the gel has set. Thus removed, the comb is inverted to the position shown in the drawings, and the apparatus is ready to be loaded with samples for electrophoresis.

The foregoing is offered primarily for purposes of illustration. It will be readily apparent to those skilled in the art that the materials, shapes, configurations and other parameters of the comb as well as the electrophoresis apparatus in which it is used may be further modified or substituted in various ways without departing from the spirit and scope of the invention.

What is claimed is:

1. A device for facilitating sample placement and defining lanes in a slab gel of a preselected thickness for the electrophoresis of a plurality of samples therein, said device comprising a rigid member of material having an edge with a series of regularly spaced projections extending therefrom, each projection terminating in a sharp point, said rigid member being constructed of a rigid metallic core sheathed in a coating of electrically insulating material which is inert to aqueous acids and bases.

2. A device in accordance with claim 1 in which said rigid metallic core is of a member selected from the group consisting of aluminum, stainless steel, copper and nickel.

3. A device is accordance with claim 1 in which said rigid metallic core is aluminum.

4. A device in accordance with claim 1 in which said rigid metallic core is an anodized metal.

5. A device in accordance with claim 1 in which said rigid metallic core is anodized aluminum.

6. A device in accordance with claim 1 in which said electrically insulating material is a polymeric material.

7. A device in accordance with claim 1 in which said electrically insulating material is a polymeric material applied to said rigid metallic core by vapor-phase polymerization.

8. A device in accordance with claim 1 in which said electrically insulating material is a polymer of p-xylylene or a derivative thereof.

9. A device in accordance with claim 1 in which said rigid metallic core is anodized aluminum, and said electrically insulating material is a polymer of p-xylylene or a derivative thereof.

* * * * *